United States Patent [19]

Kawamata et al.

[11] 4,227,023

[45] Oct. 7, 1980

[54] PROCESS FOR THE SELECTIVE ORTHO-ALKYLATION OF PHENOLIC COMPOUNDS

[75] Inventors: Motoo Kawamata, Yokohama; Tadamitsu Kiyoura, Kamakura; Kazushi Ohshima, Yokohama; Yasuo Kogure, Yokohama; Akihide Kudoh, Yokohama; Makoto Kotani, Yokohama, all of Japan

[73] Assignee: Mitsui Toatsu Chemicals, Incorporated, Tokyo, Japan

[21] Appl. No.: 966,356

[22] Filed: Dec. 4, 1978

[30] Foreign Application Priority Data

Dec. 13, 1977 [JP] Japan ................................ 52-148758

[51] Int. Cl.³ ........................ C07C 37/14; C07C 39/06
[52] U.S. Cl. ...................................... 568/804; 568/794
[58] Field of Search .............................. 568/804, 794

[56] References Cited

U.S. PATENT DOCUMENTS

| | | | |
|---|---|---|---|
| 2,448,942 | 9/1948 | Winkler et al. | 568/804 |
| 3,971,832 | 7/1976 | Watanabe | 568/804 |
| 3,974,229 | 8/1976 | Van Sorge | 568/804 |
| 4,041,085 | 8/1977 | Frabetti | 568/804 |

*Primary Examiner*—Werren B. Lone

[57] ABSTRACT

This invention relates to a process for the selective ortho-alkylation of a phenolic compound having at least one ortho-positioned a hydrogen atom by catalytically reacting the phenolic compound with an alcohol in the vapor phase. In this process, the reaction of the phenolic compound with the alcohol is carried out at a temperature of from 300° to 550° C. in the presence of a mixed oxide catalyst of manganese, silicon, and one or more additives selected from the group consisting of magnesium oxide, calcium oxide, strontium oxide, and barium oxide. The catalyst used in this invention exhibits not only excellent catalytic activity in the selective ortho-alkylation of phenols but also continuous stability of the activity, good shapability, and good mechanical strength.

4 Claims, No Drawings

PROCESS FOR THE SELECTIVE ORTHO-ALKYLATION OF PHENOLIC COMPOUNDS

BACKGROUND OF THE INVENTION

This invention is concerned with a process for the selective ortho-alkylation of a phenolic compound by catalytically reacting the phenolic compound with an alcohol in the vapor phase.

The preparation of 2,6-dimethylphenol, among other ortho-alkylated phenols, has heretofore been the subject of many studies, because it is useful as a raw material for the manufacturing of polyphenylene oxide having a wide range of utility in the fields of synthetic resins.

Currently, a process for the ortho-alkylation of phenols in a industrial use involves the vapor phase reaction of a phenol with an alcohol in the presence of a solid acid catalyst such as alumina. However, in this process, the selectivity for the ortho-alkylation is insufficient. That is, the meta and para positions of the phenol as well as the ortho positions thereof are alkylated to a considerable extent, so that a complicated procedure for the separation and purification of the ortho-alkylated product is required.

Another industrial process is based on the use of a magnesium oxide catalyst. But, this catalyst has inherently low activity, so that it requires reaction temperatures higher than 475° C., practically higher than 500° C., to perform the reaction sufficiently. Moreover, the life of the catalyst is not long enough, so the regeneration is required in a relatively short period of time for practical use.

In order to solve these problems, there have been proposed many kinds of catalysts; for example, those comprising various combinations of magnesium oxide and other oxides, or those comprising various combinations of iron oxide and other components.

These catalyst combinations, however, still have similar disadvantages those mentioned above, namely either they are insufficient in selectivity for ortho-alkylation and in service life or they induce the alkylation of undesired positions (other than the ortho positions) and the formation of polyalkylated products under such reaction conditions as to produce a satisfactorily high catalytic activity.

Meanwhile, a process for the selective ortho-alkylation of a phenolic compound having at least one ortho-positioned hydrogen atom by using a maganese oxide catalyst is disclosed in U.S. Pat. No. 3,971,832. The invention disclosed therein relates to a process for the ortho-methylation of a phenol which comprises contacting the vaporized phenol with an alcohol at a temperature of from 250° C. to 500° C. in the presence of a catalyst consisting essentially of trimanganese tetroxide previously calcined at a temperature of from 950° C. to 1,500° C. It is stated that one feature of the invention is to provide a process for the ortho-methylation of phenols with a very high degree of selectivity under mild reaction conditions. However, this process does not succeed in providing sufficiently high degrees of conversion of the phenol and selectivity for O-cresol or 2,6-xylenol. Moreover, in order to obtain a high catalytic activity in this process, a manganese compound must be converted to trimanganese tetroxide by preheating it to a temperature higher than 950° C.

The present inventors made extensive studies for the purpose of overcoming the difficulties encountered in the aforesaid prior art process, and discovered that a mixed oxide catalyst of manganese and silicon is effective for the selective ortho-alkylation of phenols and that the activity of this catalyst is much prolonged as compared with prior art catalysts. The invention based on this discovery is described and claimed in Japanese Patent Application No. 97874/77, which relates to a process for ortho-methylating a phenol by reacting the phenol with methyl alcohol in the presence of a mixed oxide catalyst of manganese and silicon.

BRIEF SUMMARY OF THE INVENTION

It is an object of the present invention to provide an improved process for the selective ortho-alkylation of a phenolic compound having at least one ortho-positioned hydrogen atom by catalytically reacting the phenolic compound with an alcohol in the vapor phase.

It is another object of the present invention to provide a catalyst which is capable of carrying out the aforesaid selective ortho-alkylation reaction, the catalyst exhibiting not only enhanced catalytic activity but also excellent characteristics as required for industrial catalysts, such as good shapability and high mechanical strength.

These and other objects of the present invention will become more apparent from the following detailed description and examples.

According to the present invention, there is provided a process for the selective ortho-alkylation of a phenolic compound having at least one ortho-positioned hydrogen atom by catalytically reacting the phenolic compound with an alcohol in the vapor phase, wherein the improvement comprises carrying out the reaction in the presence of a mixed oxide catalyst of manganese and silicon, and one or more additives selected from the group consisting of mangnesium oxide, calcium oxide, strontium oxide, and barium oxide.

DETAILED DESCRIPTION OF THE PREFERRED EMBODIMENTS:

The phenolic compound which is used in the practice of the invention is one having at least one ortho-positioned hydrogen atom and can be represented by the general formula

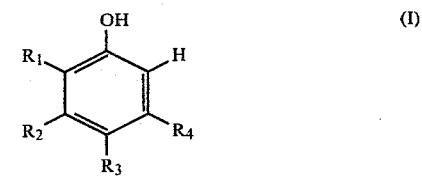

where $R_1$, $R_2$, $R_3$ and $R_4$ independently represent hydrogen atoms or aliphatic hydrocarbon groups such as methyl, ethyl, n-propyl, iso-propyl, n-butyl, iso-butyl, and tert-butyl, groups. Specific examples of the phenolic compound include phenol; o-, m- and p-cresols; 2,3-, 2,4-, 2,5-, 3,4- and 3,5-xylenols; trimethyl-phenols; n- and iso-propylphenols; n-, iso- and tert-butylphenols; and the like. Phenolic compounds having two or more different alkyl substituent groups on the same aromatic nucleus are also useful.

The alcohol which is used in the practice of the invention is a saturated aliphatic alcohol having from 1 to 4 carbon atoms. Specific examples of the alcohol include methyl alcohol, ethyl alcohol, iso-propyl alcohol, n-propyl alcohol, n-butyl alcohol, iso-butyl alcohol, tert-butyl alcohol, and the like.

The mixed oxides catalyst which is used in the process of the invention consists of manganese, silicon, and one or more additives selected from the group consisting of magnesium oxide, calcium oxide, strontium oxide, and barium oxide. The manganese oxide and silicon oxide contained in this catalyst are present in such a proportion as to provide an atomic ratio of manganese to silicon ranging from 100:0.01 to 100:20 and preferably from 100:0.05 to 100:10. The third component, which comprises one or more additives selected from the group consisting of magnesium, calcium, strontium and barium, is present in such an amount as to provide at atomic ratio of manganese to additive metals ranging from 100:0.01 to 100:30 and preferably from 100:0.05 to 100:20. This third component serves not only to retain the initial activity of the catalyst over an extended period of time but also to suppress the formation of undesired reaction products such as p-cresol, 2,4-xylenol and 2,4,6-trimethyl phenol. Additionally, the catalyst containing this third component exhibits good shapability when it is subjected to pelletization, extrusion and other techniques. As a result, the catalyst of the invention not only is efficiently formed into any desired shape but also has such high strength in the course of shaping, calcining and reaction that the degree of breakage is much reduced when it is packed into a reactor and used in the reaction. However, if the amount of the third component exceeds the aforesaid upper limit, the activity of the catalyst tends to diminish and the strength of the catalyst begins to decrease adversely.

The manganese compounds from which the manganese oxide can be derived include, for example, manganese hydroxide, manganese carbonate, manganese nitrate, manganese sulfate, manganese chloride, and the like. The silicon compounds from which the silicon oxide can be derived include, for example, silicic acid, silicic anhydride, metallic salts of silicic acid, silicon tetrachloride, organosilicon compounds, and the like. The alkaline earth metal oxide or oxides which constitute the third component of the catalyst can be derived, for example, from the nitrates, hydroxides, sulfates, halides and carbonates of the respective metals.

A number of methods are available for the preparation of the catalyst. For example, it may be prepared either by adding a small amount of water to a mixture of various compounds as described above and blending the mixture well in a kneader or mixer, or by adding a suitable precipitating agent to an aqueous solution of various compounds and separating the coprecipitated insoluble product. It is also possible to form a mixed oxide of manganese and silicon from suitable compounds at first, and then add an alkaline earth metal oxide or oxides thereto. Usually, the resulting catalyst is dried at a temperature below 150° C., calcined at a temperature of from 300° to 900° C. (which step may be omitted if desired), and then shaped by any conventional method to form a catalyst ready for use. Alternatively, it may be coated on a suitable carrier such as alumina, silica, steatite, carborundum, or the like and then calcined, until ready for use.

In carrying out the process of the invention, a phenolic compound and an alcohol are mixed in a molar ratio ranging from 1:1 to 1:15 and preferably from 1:1 to 1:6. Prior to being fed the to the reaction zone, these starting materials may be diluted with a suitable inert gas such as nitrogen or carbon dioxide to make the reaction proceed smoothly. Furthermore, it is also effective to introduce a small amount of water with the reactants into the reaction zone. The presence of such water serves not only to prolong the service life of the catalyst but also to suppress any undesirable decomposition of the alcohol.

The process of the invention is carried out at a temperature of from 300° C. to 550° C. and preferably from 350° to 500° C. If the reaction temperature is higher, the selectivity for ortho-alkylation is reduced and the formation of various high-boiling products is increased. On the other hand, if the reaction temperature is lower, the conversion of the reactants is insufficient for the practical use, as a result, great amounts of unreacted starting materials or intermediate products must be recovered and recycled.

The reactants are preferably fed to the reaction zone at a gas space velocity of from 300 to 20,000 per hour. Generally speaking, greater gas space velocities are suitably used for reactions at higher temperature, and vice versa. The reaction may be carried out under a pressure higher or lower than atmospheric pressure. The reaction may be carried out according to any of the fixed bed, fluidized bed, and moving bed processes.

The present invention is further illustrated by the following examples.

EXAMPLE 1

One thousand g of manganese nitrate hexahydrate was heated to 40° C. On the other hand, 21 g of sodium silicate containing 30% silicic anhydride ($SiO_2$) and 10% sodium oxide ($Na_2O$), was diluted with 100 ml of water and then added it drop by drop to the above manganese solution, whereby a precipitate of silica gel was formed. The resulting manganese solution containing silica gel was diluted with 10 l of water, and aqueous ammonia was added thereto until its pH reached 9.

To the coprecipitant, 7.5 g of calcium hydroxide was added. After adequate stirring, the mixture was decanted washed with water and filtered. The filter cake was dried in hot air at 150° C. for 10 hours and ground to fine powder. Using a pelletizing machine, the resulting powder was formed into pellets having a diameter of 4 mm and a height of 3 mm. This powder exhibited a good shapability. Then, these pellets were calcined at 500° C. for 10 hours to form a mixed oxide catalyst of manganese, silicon, and calcium. The resulting catalyst had a crushing strength of about 7 kg. Because of this sufficiently high mechanical strength, no special consideration was required in packing it into a reactor.

Then, 100 ml of this catalyst was packed into a stainless steel tubular reactor having an internal diameter of 25 mm and heated to 430° C. Thereafter, a mixture of phenol and methanol (a molar ratio of 1:4) was vaporized at 300° C., and then introduced into the reactor at a rate of 60 g per hour.

The reaction product was cooled by a water-cooled condenser and then collected in a dry ice-acetone trap. The product thus obtained was analyzed by gas chromatography. The results are summarized in Table 1. After using the catalyst in the above reaction, all the pellets were found to retain their original shape.

CONTROL 1

Using the same procedure of Example 1, manganese hydroxide and silica gel were coprecipitated, washed with water, and filtered. The filter cake was dried in hot air at 150° C. for 10 hours and ground to fine powder. Using a pelletizing machine, the resulting powder was formed into pellets having a diameter of 4 mm and a height of 3 mm. Shapability of this powder is insufficient, so that part of the pellets were out of shape. Then, these pellets were calcined at 500° C. for 10 hours to form a mixed oxide catalyst of manganese and silicon. The resulting catalyst had a crushing strength of about 0.6 kg. Because of this low mechanical strength, much care was required in packing it into a reactor.

This catalyst was tested in the same manner as described in Example 1. The pressure drop of the catalyst bed, which was 2.0 mm Hg at the beginning of the reaction, rose as time went on and reached 12 mm Hg at the end of 100 hours. After the reaction, about one-third of the pellets were found to be more or less out of shape.

Table 1

| Results | Catalyst (atomic ratio) | |
|---|---|---|
| | Example 1 (Mn:Si:Ca = 100:2.01:1.87) | Control 1 (Mn:Si = 100:2.01) |
| After 5 Hours of Reaction | | |
| Conversion of Phenol (%) | 99.8 | 99.2 |
| Selectivity for o-Cresol (%) | 2.7 | 3.8 |
| Selectivity for 2,6-Xylenol (%) | 95.5 | 94.5 |
| Selectivity for 2,4-Xylenol (%) | 0.1 | 0.2 |
| Selectivity for 2,4,6-Trimethylphenol (%) | 1.7 | 1.5 |
| After 100 Hours of Reaction | | |
| Conversion of Phenol (%) | 99.9 | 90.5 |
| Selectivity for o-Cresol (%) | 2.1 | 12.9 |
| Selectivity for 2,6-Xylenol (%) | 96.4 | 85.5 |
| Selectivity for 2,4-Xylenol (%) | 0.0 | 0.6 |
| Selectivity for 2,4,6-Trimethylphenol (%) | 1.5 | 1.0 |

EXAMPLE 2

The procedure of Example 1 was repeated using magnesium hydroxide in place of calcium hydroxide. The resulting catalyst, in the form of pellets having a diameter of 4 mm and a height of 3 mm, exhibited as good shapability as that of Example 1 and had a crushing strength of 4 kg.

Using 100 ml of this catalyst, the reaction was carried out in the same manner as described in Example 1. After 80 hours of reaction, the conversion of the phenol was 100%. The selectivity was 2.0% for o-cresol, 96.5% for 2,6-xylenol, 0.01% for 2,4-xylenol, and 1.5% for 2,4,6-trimethylphenol.

EXAMPLES 3-9

Catalysts, having various compositions, were prepared in the same manner as described in Example 1. Using these catalyst packed into a reactor similar to that used in Example 1, the reaction was carried out at different temperatures. The results are summarized in Table 2.

Table 2

| Example No. | Composition of Catalyst (Mn:Si:Ca atomic ratio) | Reaction Temperature (°C.) | Conversion of Phenol (%) | Selectivity for 2,6-Xylenol (%) |
|---|---|---|---|---|
| 3 | 100:1:1.2 | 430 | 99.8 | 96.3 |
| 4 | 100:2:3.5 | 430 | 99.5 | 95.4 |
| 5 | 100:2:5.8 | 430 | 99.7 | 94.7 |
| 6 | 100:2:5.8 | 460 | 99.9 | 93.1 |
| 7 | 100:8:7.5 | 450 | 98.4 | 93.8 |
| 8 | 100:16:12.7 | 470 | 98.9 | 90.9 |
| 9 | 100:3:18 | 440 | 99.0 | 93.5 |

Many widely different embodiments of the present invention may apparently be made without departing from the spirit and scope thereof. However, it is to be understood that the present invention is not limited to the specific embodiments thereof except as defined in the appended claims.

What is claimed is:

1. In a process for the selective orthoalkylation of a phenolic compound having at least one orthopositioned hydrogen atom and having the general formula

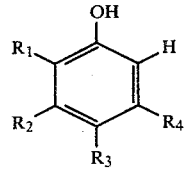

wherein $R_1$, $R_2$, $R_3$ and $R_4$ represent hydrogen atoms or aliphatic hydrocarbon radicals, by catalytically reacting the phenolic compound with a saturated aliphatic alcohol having from 1 to 4 carbon atoms, in the vapor phase, the improvement which comprises carrying out the reaction at at a temperature of from 300° C. to 500° C. with a molar ratio of phenolic compound to alcohol ranging from 1:1 to 1:15 in the presence of a catalyst consisting of manganese oxide, silicon oxide and one or more oxides selected from the group consisting of magnesium oxide, calcium oxide, strontium oxide and barium oxide, said manganese and silicon contained in the mixed oxide catalyst being present in such a proportion as to provide an atomic ratio of manganese to silicon ranging from 100:0.01 to 100:20 and said one or more oxides selected from the group consisting of magnesium oxide, calcium oxide, strontium oxide and barium oxide being present in such an amount as to provide an atomic ratio of magnesium to additive metals ranging from 100:0.01 to 100:30.

2. A process as claimed in claim 1 wherein the phenolic compound having at least one ortho-positioned hydrogen atom is phenol and/or o-cresol.

3. A process as claimed in claim 1 wherein the alcohol is a lower saturated aliphatic alcohol having from 1 to 4 carbon atoms.

4. A process as claimed in claim 1 wherein the alcohol is methyl alcohol.

* * * * *